United States Patent
Maier et al.

(10) Patent No.: US 7,729,794 B2
(45) Date of Patent: Jun. 1, 2010

(54) METHOD FOR DESIGNING A CONNECTOR

(75) Inventors: Martin Maier, Bad Gandersheim (DE); Alexander Hilbert, Rodgau (DE)

(73) Assignee: Degudent GmbH, Hanau (DE)

( * ) Notice: Subject to any disclaimer, the term of this patent is extended or adjusted under 35 U.S.C. 154(b) by 287 days.

(21) Appl. No.: 11/856,888

(22) Filed: Sep. 18, 2007

(65) Prior Publication Data

US 2008/0077270 A1 Mar. 27, 2008

(30) Foreign Application Priority Data

Sep. 27, 2006 (EP) .................................. 06020237

(51) Int. Cl.
G06F 17/50 (2006.01)
A61C 13/38 (2006.01)
(52) U.S. Cl. ........................... 700/118; 433/213; 433/1; 433/190; 700/163; 700/182
(58) Field of Classification Search ................. 700/118; 433/1, 190; 359/458; 382/154
See application file for complete search history.

(56) References Cited

U.S. PATENT DOCUMENTS

| | | | | | |
|---|---|---|---|---|---|
| 5,257,203 | A | * | 10/1993 | Riley et al. | 700/163 |
| 6,049,743 | A | * | 4/2000 | Baba | 700/163 |
| 6,694,212 | B1 | * | 2/2004 | Kennedy | 700/163 |
| 7,247,021 | B2 | * | 7/2007 | Jones et al. | 433/213 |
| 2008/0131846 | A1 | * | 6/2008 | Marshall et al. | 433/218 |

FOREIGN PATENT DOCUMENTS

| | | | |
|---|---|---|---|
| WO | WO 99/47065 | * | 9/1999 |
| WO | WO 03/007834 | * | 1/2003 |
| WO | WO 2006077267 | * | 7/2006 |

OTHER PUBLICATIONS http://web.wieland-dental-systems.com/uploads/tx_pxwldownloads/DentalDesigner_GB.pdf, Dental designer, 2007, pp. 50-66.*
An Tao et al, Computer Aided Design and Manufacturing of the Framework of PFM Fixed Bridge, Nov. 2006, pp. 1-5.*
Wolfgang, A Survey of curve and surface methods in CAGD 1983, pp. 1-61.*

* cited by examiner

Primary Examiner—Ramesh B Patel
Assistant Examiner—Olvin Lopez
(74) Attorney, Agent, or Firm—Dennison, Schultz & MacDonald

(57) ABSTRACT

A method for designing a connector between a first and a second element of a dental restoration, such as a connector between coping and coping, or coping and pontic, or pontic and pontic of a bridge, which is characterized by the steps of computing a (first) model of the first element and a (second) model of the second element, defining a connecting straight line between the first model and the second model, computing edge curves ($\gamma 0$, $\gamma 4$) on the first model and the second model, whereby the edge curves are defined by origins of surface normal vectors of the models, which satisfy boundary conditions relative to the connecting line, computing offset curves ($\gamma 1$, $\gamma 3$) on the first model and the second model from the first edge curves, and connecting the first edge curves and the offset curves of the first model and of the second model and computing the connector on the basis of the course of the connection between the curves.

21 Claims, 8 Drawing Sheets

Modeling the tangential transition from the connector curve to the ring model (coping)

METHOD FOR DESIGNING A CONNECTOR

BACKGROUND OF THE INVENTION

The invention relates to a method for designing a connector between a first and a second element of a dental restoration, such as a connector between a cap (coping hereinafter) and a coping, or a coping and an intermediate element (pontic hereinafter), or a pontic and a pontic of a bridge.

Dental restorations are increasingly produced using CAD/CAM processes. For this, physical models of stumps are scanned and the distribution of measured points subsequently is used to compute models, which are then used in the manufacturing of the dental prosthesis. In this regard, we refer to WO-A-99/47065 and WO-A-03/07834 as examples.

With regard to copings, the respective methods yield extremely satisfactory results. However, the production of connectors poses problems. Thus, state of the art connectors are characterized by quasi-standardized geometries, which consist of tubular sections that are rounded at the ends to be connected to the copings or pontics. If using a hob cutter for this, the ends can be blocked out in order to remove edges.

U.S. Pat. No. 6,049,743 discloses a method for designing dental prostheses such as bridges and crowns. Here, the particular data of a set of teeth is recorded and taken into account when selecting one of a number of stored bridge elements for the dental prosthesis.

A method for fitting a digital set of 3D data of a dental prosthesis element to neighbouring teeth is known from DE-A-10 2005 009 873 (=WO-A-2006/077267), whereby a contact area to the adjacent teeth is defined.

U.S. Pat. No. 5,257,203 describes a method for manipulating a computer-controllable 3D model with ideal geometry to match actual conditions.

SUMMARY OF THE INVENTION

The objective of the present invention is to provide a connector for a dental restoration that possesses an anatomically correct shape and is custom-matched to the positions and geometries of the individual elements to be connected.

As a solution to meet this objective, we propose a method for designing a connector between a first and a second element of a dental restoration that is characterized by:

Computing a (first) model of the first element and a (second) model of the second element, defining a connecting straight line between the first model and the second model, computing edge curves ($\gamma 0$, $\gamma 4$) on the first model and the second model, whereby the edge curves are defined by the origins of surface normal vectors of the models, which adhere to boundary conditions relative to the connecting straight line, computing offset curves ($\gamma 1$, $\gamma 3$) on the first model and the second model from the first edge curves, and connecting the first edge curves and the offset curves of the first model and the second model and computing the connector on the basis of the course of the connection between the curves.

According to the invention, the geometrical parameters of the elements to be connected are taken into account in the design of the connector, i.e. one commences by generating data and then uses these data in a CAD/CAM process to manufacture the connector together with the elements. Digitized values of the elements are taken into account and are used to compute models that are needed in the design calculation for the connector.

In accordance with the invention's instructions, the following method is implemented:

Scanning a physical model such as of a stump, computing a three-dimensional model from the distribution of measured points acquired by scanning, computing from the three-dimensional model a three-dimensional model of the coping as the first or second model, parameterizing the three-dimensional model of the coping in a two-dimensional parameter space, in which each point corresponds to an X, Y, Z coordinate and a normal vector in the three-dimensional space of the coping, and determining the first edge curve from the parameterized two-dimensional space, or computing a three-dimensional model as the first or second model of a pontic selected from a data library, parameterizing the three-dimensional model in a two-dimensional parameter space, in which each point corresponds to a X, Y, Z coordinate and a normal vector in the three-dimensional space, and determining the edge curve from the parameterized two-dimensional space.

In this manner, simple procedures are adequate to determine or compute the edge curves while also taking into account the boundary conditions, whereby as a boundary condition for the location of the surface normal defining the edge curve one specifies an angle $\alpha$ between the connecting straight line and the surface normal. In particular, $\alpha \leqq 90°$. The particular boundary condition that depends on the angle $\alpha$ is sufficient for the determination of the contact surface between the connector and the first or second element in cases where the element's surface shape exhibits a smooth behaviour to such an extent that depressions such as grooves or dents are not present. If surface contours that must be referred to as irregularities are present, for which the surface normal encloses with the connecting straight line an angle $\alpha$ with $\alpha \geqq 90°$, one specifies as boundary condition for the position of the origin of the surface normal both the angle $\alpha$ between the surface normal and the connecting straight line as well as an angle $\beta$.

The angle $\beta$ extends between the connecting straight line and a line connecting the origin of the surface normal to a characteristic parameter of the first or second element, in particular the centroid. The condition $(\alpha+\beta): 2 \geqq \phi$ must be met. Upon reaching the angle $\phi$, which should be regarded as threshold value, the computation is terminated, i.e. the point in the two-dimensional parameter space for which the boundary condition $(\alpha+\beta): 2 = \phi$ is reached, will be chosen as a point of the edge curves $\gamma 0$, $\gamma 4$. $\phi$ should be in the range $30° \leqq \phi \leqq 90°$, in particular $70° \leqq \phi \leqq 90°$.

The computation is performed in a way so that on straight lines, which originate from a point in the two-dimensional parameter space that corresponds to the piercing point of the connecting line through the three-dimensional model, checks are performed on whether the specified boundary conditions are still met, and the computation is terminated once a specified boundary condition is no longer met. This point on the straight line then provides the coordinates of a point on the edge curves $\gamma 0$, $\gamma 4$.

In other words, the edge curves $\gamma 0$, $\gamma 4$ is defined by the coordinates of the origins of the normal vectors, for which the boundary condition $(\alpha+\beta): 2 \cong \phi$ is met. Points for which $(\alpha+\beta): 2 < \phi$ will be situated within the area enclosed by the edge curve to be determined and consequently points for which $(\alpha+\beta): 2 > \phi$ will be situated outside the edge curve.

As further boundary condition for the edge curves (γ0, γ4) one can specify a facing spacing to be maintained relative to the preparation margin of the first and/or second element (coping).

As further development of the invention it is intended that a third curve γ2 be determined—between the first and the second element and pierced by the connecting straight line—which is joined to the first edge curves and the offset curves and the connections obtained in this manner are used to align the direction of the connector.

If the edge curves and the offset curves, which are reduced curves of the edge curves, are used to design a tangential transition between the connector and the first or second element, whereby the reduction factor V for reducing the curves should be between $0.0 < V < 1.0$, in particular in the range $0.1 < V < 0.4$, then the additional curve γ2 determines the necessary minimum cross-section of the connector to ensure strength and modulus of elasticity.

However, it must be pointed out that taking into account a third curve γ2 is not obligatory. Rather it is possible that solely for the computation of the connector, one can specify the secondary condition that the connector between the elements to be connected must possess a minimum cross-section, which is dependent on the position and type of the elements to be connected.

Preferably, the connecting straight line itself should pass through the centroids of the first and second element or of their models, even though other characteristic quantities can also serves as reference points. For example, it is possible to determine the path from a connecting straight line intersecting the pseudo-rotation axes, or the principal axes of inertia of the elements or their models.

If a dental restoration with a pontic is to be produced, it is at first necessary to define the pontic's position within the dental restoration. For this purpose, one at first determines the jaw segment to be covered. As an aid one uses a library, which contains statistical models mapping rows of teeth as a sequence of special point coordinates for each tooth position within a Cartesian space. The values of the coordinates themselves have been determined from average positions of scanned jaw models.

If position and shape of the stumps to be furnished with the dental restoration are known, then the position of the pontic (s) can be computed, so that subsequently—starting from the corresponding computed position—the connecting straight line to the adjacent element to be connected, i.e. a further pontic or coping, can be computed.

Consequently, for the positioning of the pontics one consults a statistical model that provides the positioning centre as well as the dimension of the pontic along the direction of the jaw segment. During this, the positions of the stumps to be connected as well as their dental designations are taken into account.

The library-retrieved data of the three-dimensional pontic model are used—equivalent to the approach used for stumps—to compute a three-dimensional model, and to subsequently use parameterization to obtain a two-dimensional parameter space, as was explained above.

With regard to the stumps, it should be noted that for the purpose of determining their shape they are surveyed three-dimensionally from all sides and the points measured in this manner are subsequently combined into a point distribution. From the data acquired in this manner, one determines or computes the edge curves and offset curves in the above-described manner.

The third curve γ2 possesses a circular shape, through the centre of which passes a second centroid-connecting straight line, which extends between the centroids of the edge curves γ0, γ4. In this, one additionally performs an alignment so that the third curve is pierced by the second centroid-connecting straight line in the centre between the centroids.

Furthermore, the third curve extends in a plane that is defined by vectors that originate in the centres of additional third centroid-connecting straight lines, which extend between centroids of segments of the first edge curves.

In particular, it is intended that each edge curve be subdivided into three equal segments and that from each of the segment centroids originate one of the third centroid-connecting straight lines. A method of this type can be implemented in a simple manner, because the edge curves are parameterized curves.

Of course, it also would be possible to select the areas enclosed by the edge curves as basis for the determination of the vectors. In this case, the areas enclosed by the edge curves could be subdivided into three equal component surfaces, with their intersection point coinciding with the centroid of the area. Then, the third centroid-connecting straight lines would originate from the centroids of the equal areas.

Furthermore, the radius of the third curve γ2 should be approximately equal to one half of the sum of the average radii of the first edge curves.

It is further suggested that the gingiva side of the pontic takes into account the shape of the gingiva and maintains a minimum distance relative to the gingiva. In this, the gingiva side, which can also be referred to as the south pole of the pontic, should for hygienic and aesthetic reasons be positioned in front of—in the vestibular direction—the ridge of the gingiva.

BRIEF DESCRIPTION OF THE DRAWINGS

Further details, advantages, and features of the invention not only can be found in the claims, the characteristic features revealed therein, on their own and/or in combination, but also in the following description and explanation of embodiment examples illustrated in the figures.

DESCRIPTION OF THE PREFERRED EMBODIMENTS

The figures are used to purely schematically explain the invention's method for designing a connector between elements of a dental restoration, whereby the connector itself together with the adjoining elements in the end is produced using a state of the art CAD/CAM process.

The manufacturing can be performed in a manner as it is described in e.g. WO-A-99/47065 or WO-A-03/007834.

Figure 1:
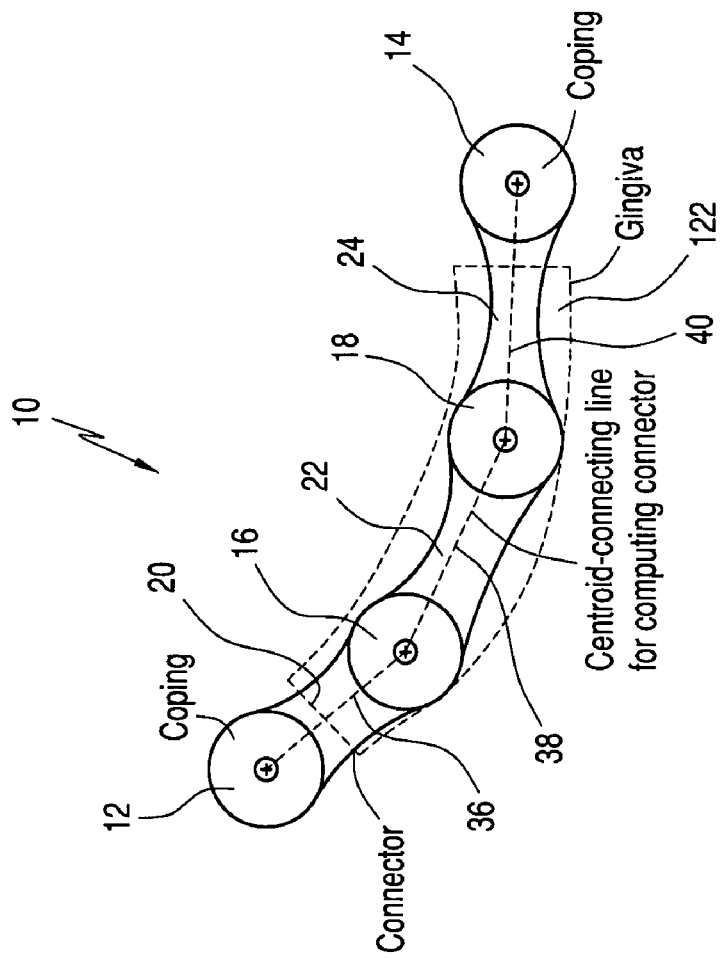
FIG. 1 shows a schematic illustration of the shape of a dental restoration to be produced.

FIG. 1 shows a top view of a four-element bridge 10 as the dental restoration to be produced. In this, the bridge comprises copings 12, 14, pontics 16, 18, as well as connectors 20, 22, 24 extending between the copings 12, 14 and pontics 16, 18, and between the pontics 16, 18 themselves. The positions of the prepared stumps to be surrounded by the copings 12, 14 is determined by moulding and subsequently scanning the stumps, or directly scanning the stumps, or scanning the positive model of the stumps. Subsequently—taking into account the known stump positions and the known section of jaw curve from a library—the positions of the pontics 16, 18 are computed with the help of a statistical model, so that the dental restoration 10 follows the shape of the jaw segment. Also retrieved from the library are data of the pontics 16, 18, so that digitalized data of their surfaces is available, which are then subjected to process measures in accordance with the explanation in the following relating to the copings 12, 14, in order to align the connectors 20, 22, 24 relative to the pontics 16, 18 and to define the transition of the outer surfaces of the connectors 20, 22, 24 to the outer surfaces of the pontics 16, 18.

Figure 2:
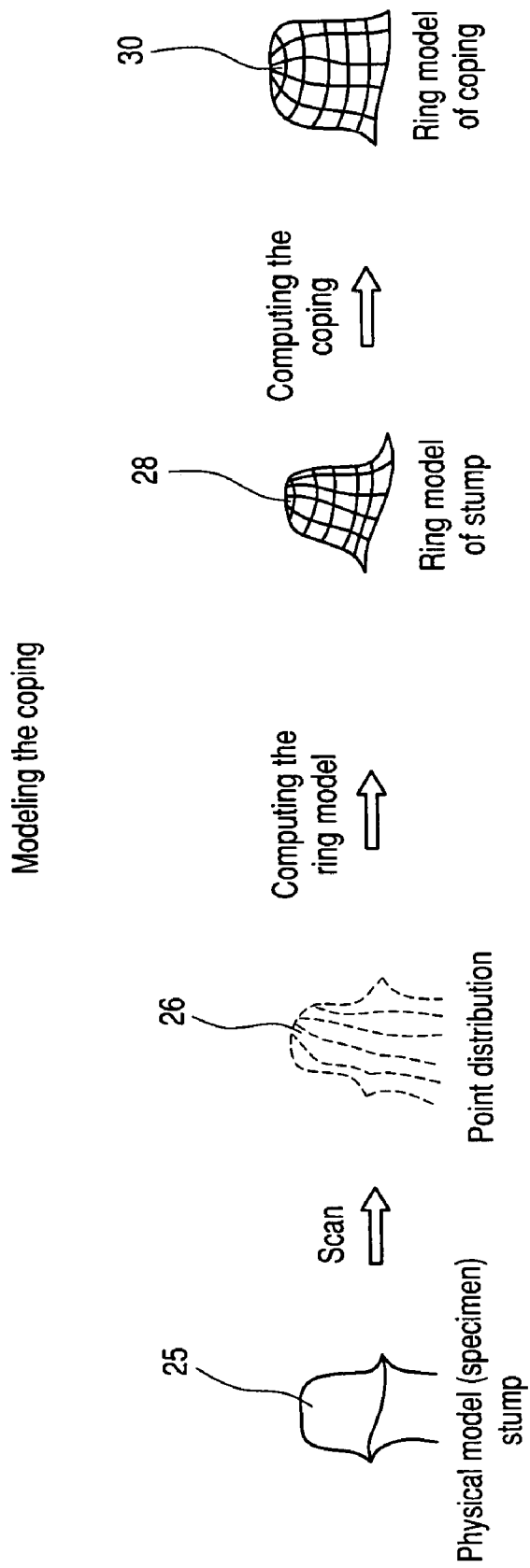
FIG. 2 shows a schematic illustration of the modelling of a coping, FIG. 3 provides explanatory illustrations for the model of FIG. 2 and its parameterization.
Figure 3:
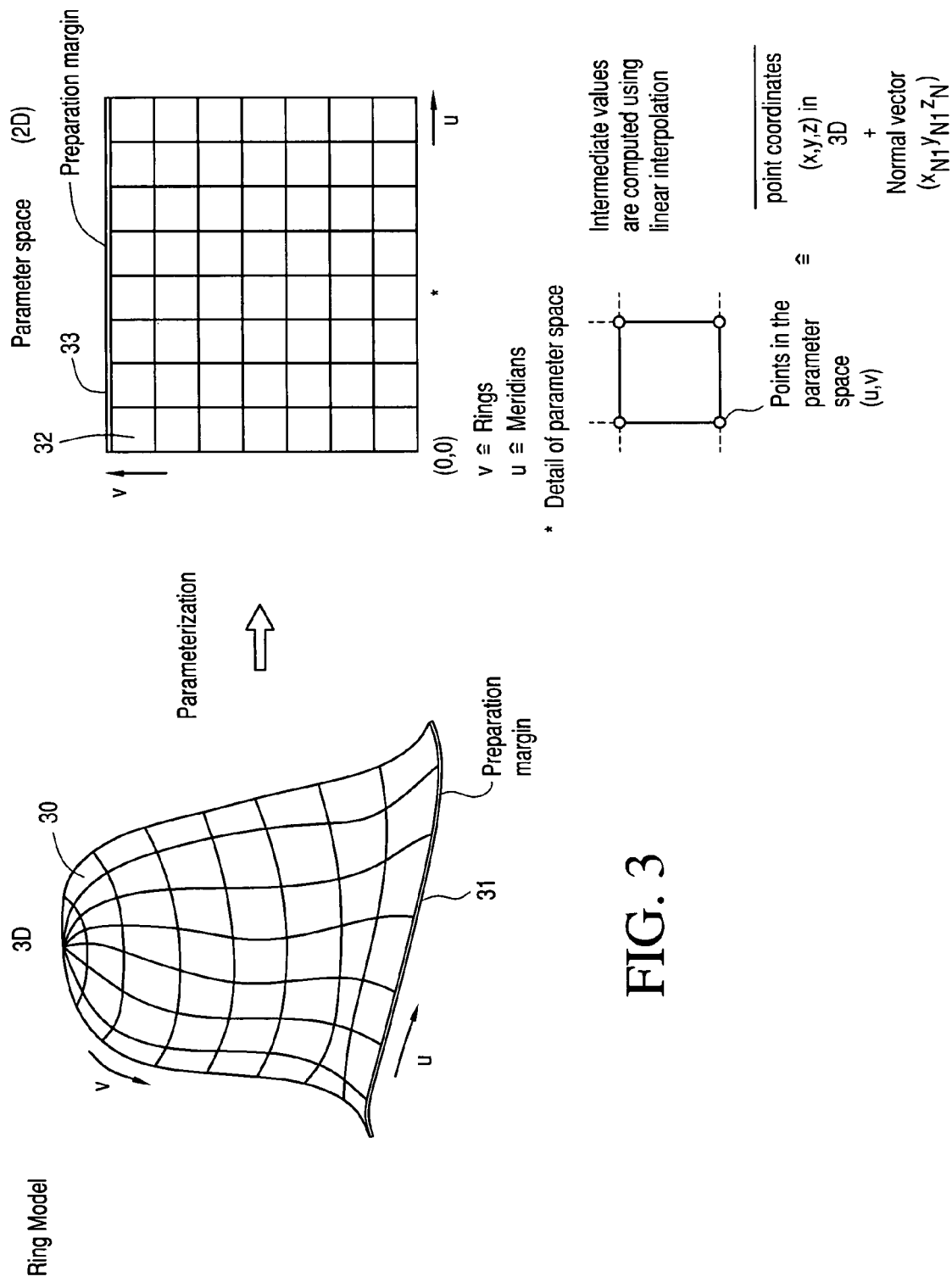

In a separate step, the stumps or physical models 25 of the stumps are scanned, whereby a three-dimensional acquisition is taken from all sides. The acquired measurement data are subsequently assembled into a point distribution. A corresponding point distribution 26 is schematically shown in FIG. 2.

The respective point distributions 26 are subsequently used to compute a three-dimensional model 28—referred to as a ring model—of the stump 25. Subsequently—taking into account a cement layer extending between the coping 12, 14 and the stump 25—one computes a three-dimensional model 30 of the coping 12, 14. This model also is referred to as ring model 30 and consists of a mesh of three-dimensional points, with rings labelled V and meridians labelled U.

A corresponding model is also used to represent the pontics or intermediate elements 16, 18 retrieved from the existing library.

Subsequently, the three-dimensional ring model 30 is parameterized in a two-dimensional parameter space 32, whereby in the graphical illustration the upper boundary 33 of the two-dimensional parameter space 32 corresponds to the preparation margin, i.e. the preparation margin 31 between the coping and the gingiva. During this ensues a parameter representation that is no longer discrete, whereby intermediate values are computed by linear interpolation. In this, every point corresponds to one X, Y, Z coordinate in the ring model 30 as well as one normal vector Xn, Yn, Zn, originating in a point on the surface of the ring model 30.

In other words, according to the invention, the surface of the coping to be produced is unwound to create a two-dimensional computational space, whereby at the same time one switches from a discrete addressability to a continuous addressability.

In order to specify the particular surface on the coping 12, 14 or the pontic 16, 18 to be manufactured, to which the connector 20, 22, 24 will be connected, the invention proceeds as follows.

The contact surface between the connector 20, 22, 24 and the coping or pontic 12, 14, 16, 18 is determined using boundary conditions for the surface normal vectors of the ring models associated with the elements, i.e. the copings 12, 14 and pontics 16, 18, which become directly apparent in the 2D parameter space 32. However, prior to that, a connecting line between the elements 12, 14, 16, 18 to be connected is specified, along which will extend the connector 22, 24 to be designed.

Figure 4:
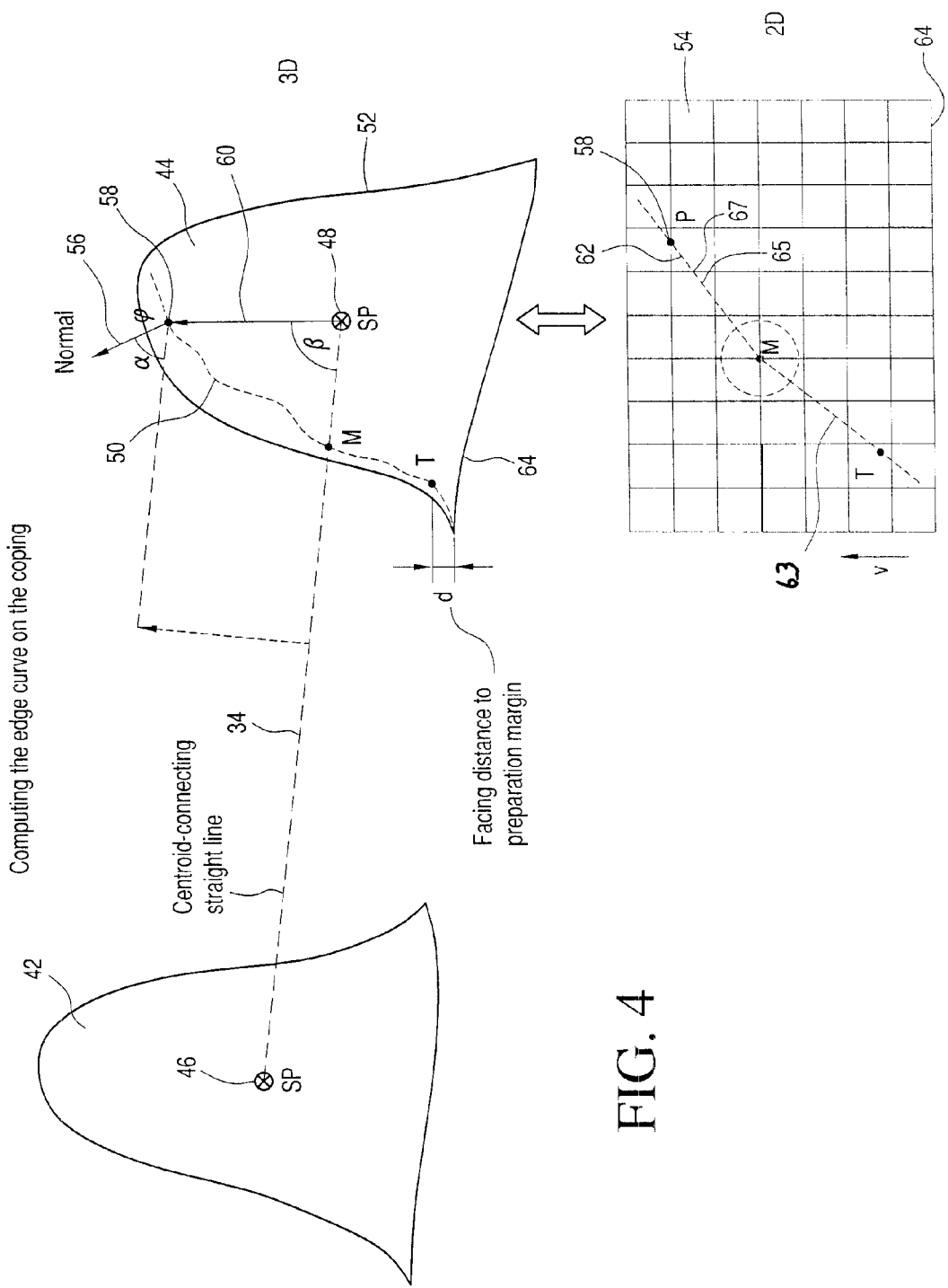
FIG. 4 shows a schematic illustration to provide an explanation of boundary conditions.

In the embodiment example the connecting straight lines are defined by straight lines 34, 36, 38, 40 that pass through the centroids of the elements 12, 14, 16, 18 to be connected. This is illustrated in FIG. 4 with the help of two three-dimensional ring models 42, 44, which represent two copings.

The straight line 34 intersects the centroids of the copings and thus the centroids 46, 48 of the models 42, 44, whereby the piercing point of the straight line 34 through the three-dimensional model 44 is labelled M. The point M is located in the dash-lined surface region 50 of the 3D model 44. The solid line 52 represents a side view of the 3D model 44. The coordinates of point M in the two-dimensional parameter space 54 are shown in FIG. 4. Subsequently one specifies in the two-dimensional parameter space 54 a curve that corresponds to an edge curve γ0 or γ4 in the ring model 42, 44 and thus on the copings associated with these, which defines the contact surface between the coping and the connector originating therefrom. For this, straight lines originating at the point M are placed into the two-dimensional parameter space 54, two of which as examples are labelled 62, 63. Subsequently, along the straight lines 62, 63 one determines at fixed intervals, which in the figure are exemplified by the individual points 65, 67 forming the straight lines 62, 63, the direction of the normal at the individual points 65, 67, in order to check whether boundary conditions are met or violated. Preferably the boundary conditions are dependent upon the angle α between the normal vector assigned to the points and the centroid-connecting straight line 34, which is offset numerically through the origin of the normal. This is illustrated in FIG. 4 with the help of point 58. Also taken into account is an angle β, extending between the centroid-connecting straight line 34 and the connection between the centroid 48 and the origin of the respective normal, i.e. in FIG. 4 between vector 60, which extends between the origin 58 of the normal 56 and the centroid 48, and the centroid-connecting straight line 34. The boundary condition is violated if $(\alpha+\beta): 2 \geq \phi$ with $\phi$ preferably $30° \leq \phi \leq 90°$, in particular $70 \leq \phi \leq 90°$. The angle β is taken into account to be able to design large contact surfaces between the connector and the coping even if the latter possess local depressions, as is illustrated in FIG. 5.

The entire two-dimensional parameter space 54 is subsequently checked for these criteria and, as edge points of the edge curve γ0, γ4 to be determined, one considers those points for which—on a straight line originating in the point M—the boundary condition $(\alpha+\beta): 2 \cong \phi$ is met. Once the condition has been fulfilled, the computation on the respective straight line is terminated and the corresponding point is selected to define the edge curve. In addition, at the lower edge, i.e. the preparation margin 64, a spacing d relative to the preparation margin must be maintained to allow a facing to be applied to the coping. This spacing d to be maintained consequently represents an additional boundary condition.

Figure 5:
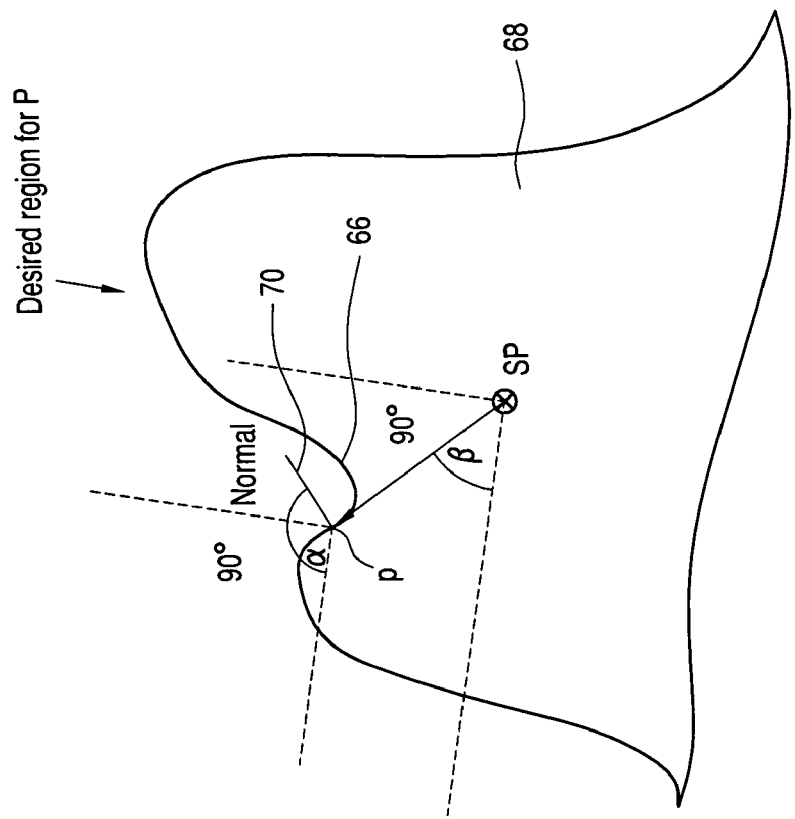
FIG. 5 shows a schematic illustration to provide an explanation of termination criteria.

FIG. 5 illustrates that the edge curve γ0, γ4 also can enclose regions of the 3D model and thus of the coping that exhibit a depression 66. As an example, the coping and thus the 3-D model 68 exhibit a depression 66, for which however the criterion $(\alpha+\beta): 2 \leq \phi$ is met, with the result that the edge curve is defined by points, which in the graphic representation are positioned on the right of the depression 66. In FIG. 5, the centroid is labelled SP and the origin of the drawn-in normal 70 is labelled P. The angles α and β correspond to those in the illustration of FIG. 4.

Once the edge curves γ0, γ4 have been determined, one computes offset curves γ1, γ3, whereby one allows for a reduction factor V with 0.0<V<1.0. Preferably the value of the factor V is between 0.1 and 0.4.

Figure 8:
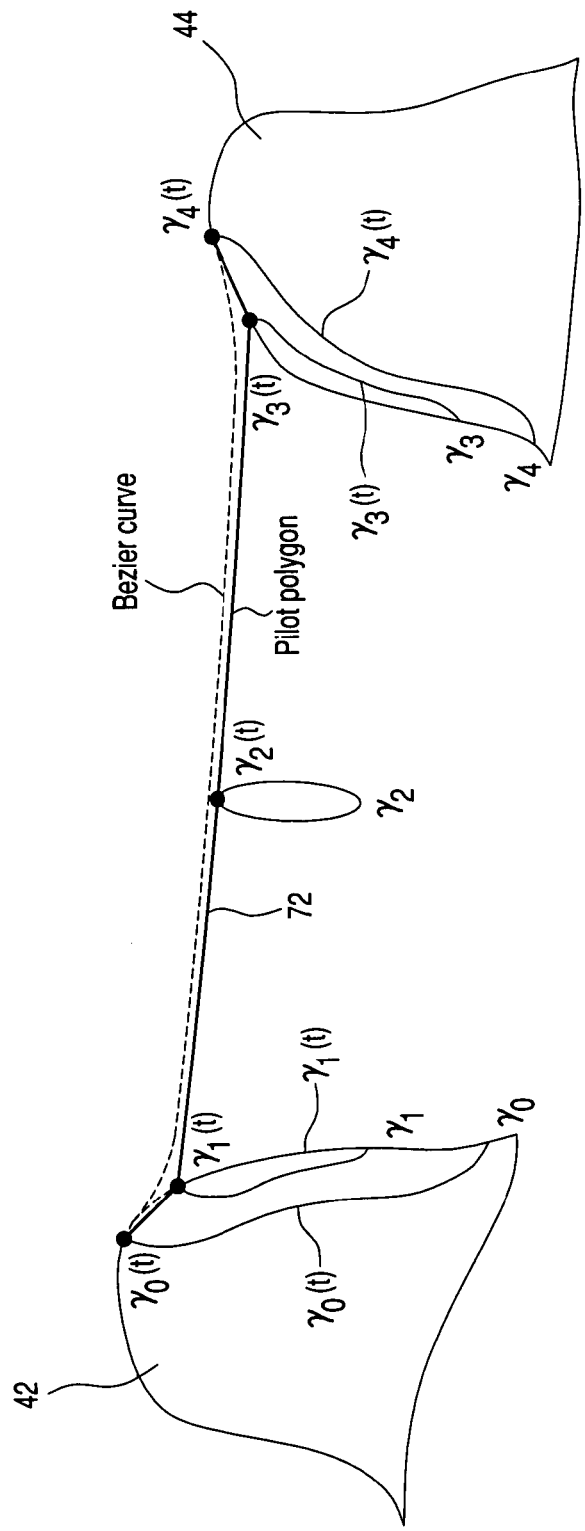
FIG. 8 shows a boundary curve of a connector.

The edge curves γ0, γ4 and the reduced curves γ1, γ3 that extend on the respective ring model 42, 44 are subsequently used in the design of the tangential transition of the connector between the ring models of stumps, or the ring model of a stump and a pontic, as will be explained in the following with the help of FIG. 8.

However, prior to that a further curve γ2 is defined, which together with the curves γ0, γ1, γ3, γ4 establishes the shape of the connector, whereby the connector is aligned on connecting lines of equal parameters between the curves γ0, γ1, γ3, γ4. The connecting lines, one of which is illustrated in FIG. 8 and labelled 72, serves as pilot polygon, along which a one-dimensionally parameterized curve such as a Bezier curve, NURBS curve, or spline curve is oriented.

Figure 6:
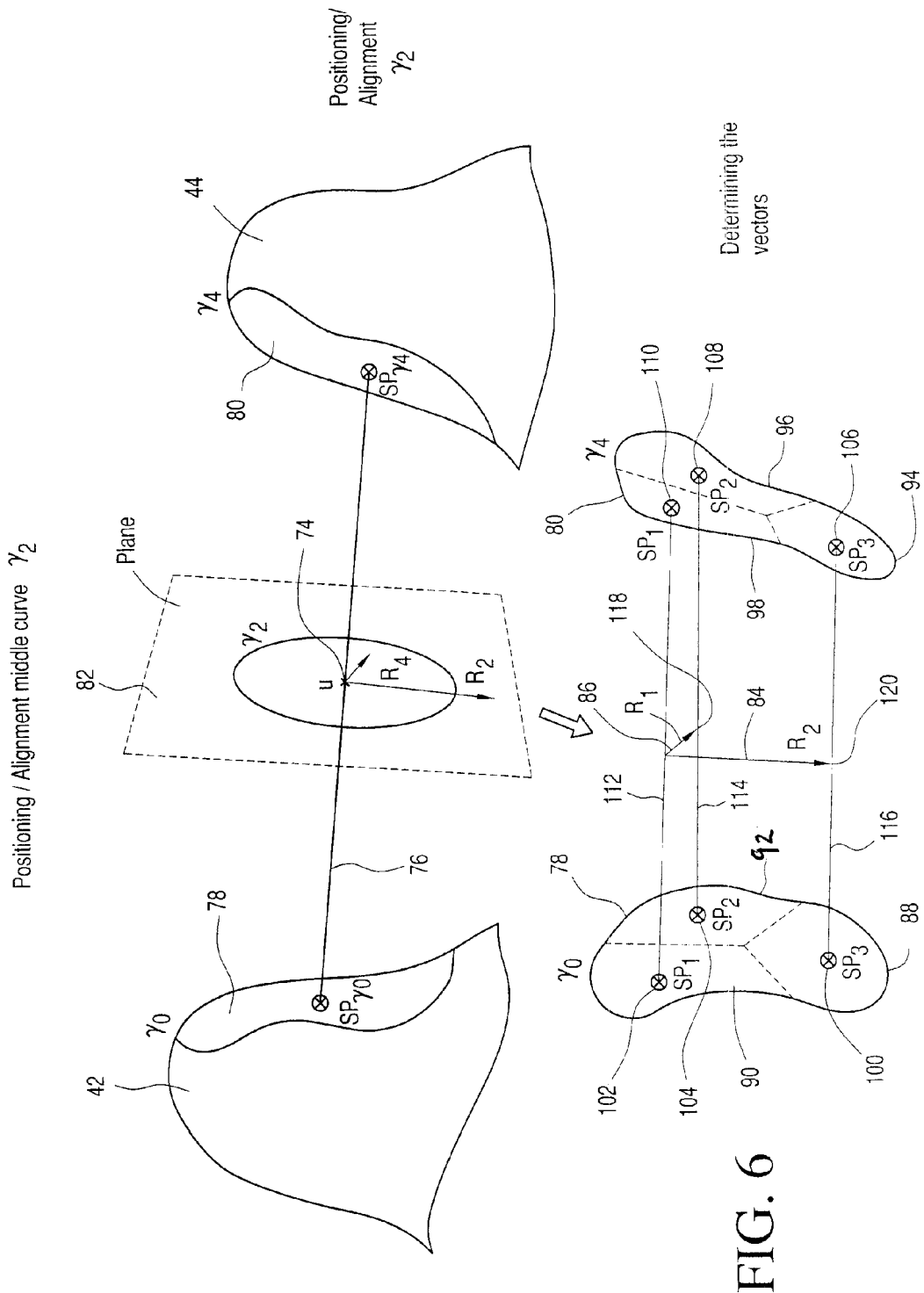
FIG. 6 shows schematic illustrations regarding the positioning of a third curve.
Figure 7:
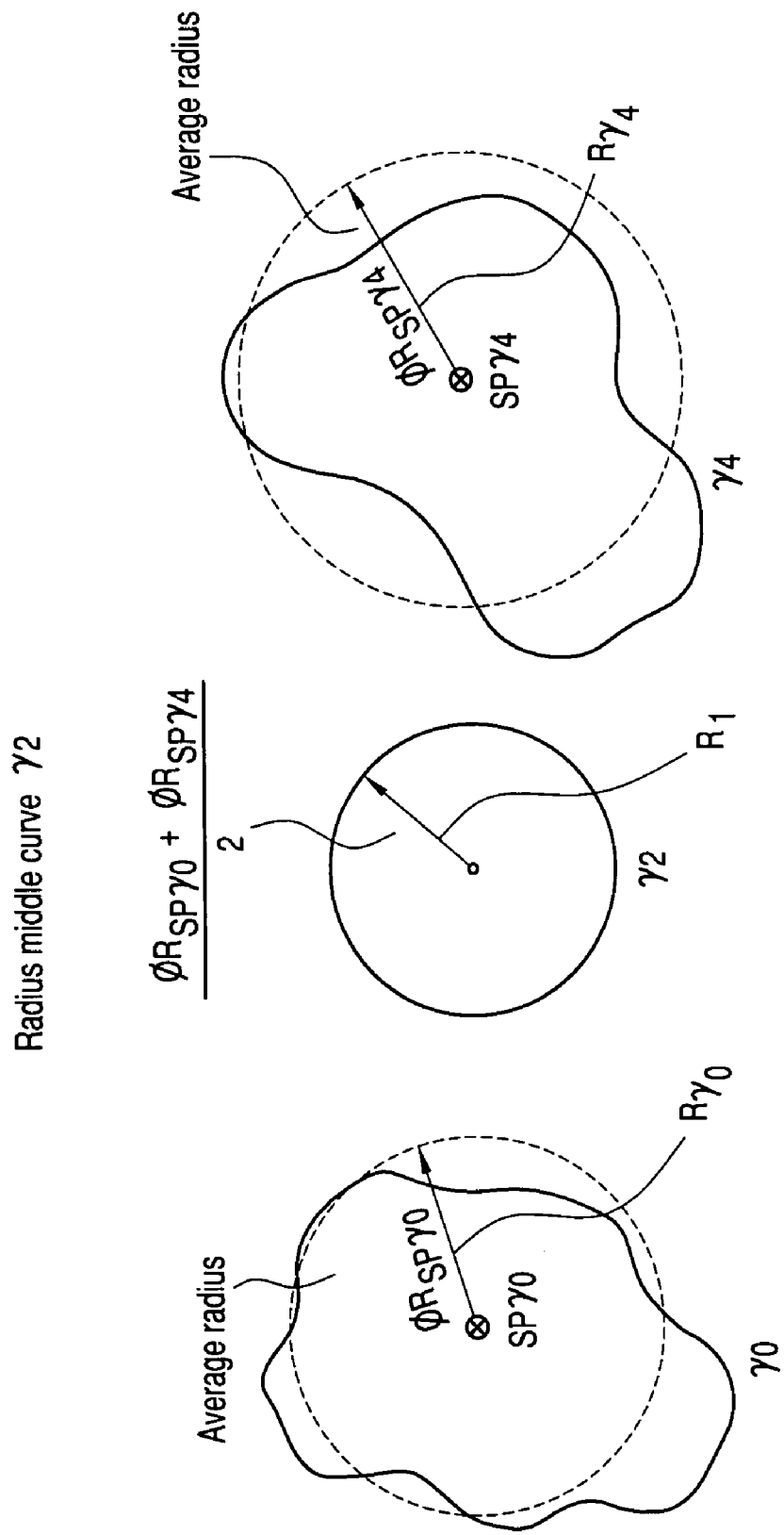
FIG. 7 shows illustrations to provide explanations of the computation of the radius of the third curve of FIG. 6.

In accordance with FIG. 6, the curve γ2 is determined in the following manner. The curve γ2 preferably is a circle, through the centre point 74 of which passes a further (second) centroid-connecting straight line 76, which originates in the centroids of the edge curves γ0, γ4 that enclose the areas 78, 80. The centre point 74 of the curve γ2 is located in the centre of the straight line 76. Furthermore, the curve γ2 is located in a plane 82, which is defined by vectors 84, 86, which are specified as follows. Each of the edge curves γ0, γ4 is subdivided into three equal segments 88, 90, 92, 94, 96, 98 in the parameter space. Subsequently, the centroid 100, 102, 104, 106, 108, 110 is computed for each segment 88, 90, 92, 94, 96. The centroids of equal segments are connected by straight lines 112, 114, 116 (third centroid-connecting straight line). Vectors 84, 86 originate from the centre of one of the straight lines 112, 114, 116 and terminate in the centre of the neighbouring straight line 114, 116. The ends of the vectors 84, 86, i.e. the points 118, 120 as well as the centre point 74 of the curve γ2 then specify their path in the plane.

Even though the curve γ2 preferably possesses a circular shape, other geometries, such as a polygon, are also possible. The computations to be performed would be accordingly different. The third centroid-connecting straight lines can also be determined by an approach that does not divide the edge curves γ0, γ4 into segments of equal length, but rather divides the areas 78, 80 enclosed by the edge curves γ0, γ4 into three equal parts, whereby the point of intersection of the three equal areas is located in the centroid of the areas 78, 80. Then the centroids of the component areas of the areas 78, 80 are connected in order to define the third centroid-connecting straight line.

However, the computation via the edge curves γ0, γ4 is simple, since one is dealing with parameterized curves.

The radius R1 of the curve γ2 is determined by computing average radii R γ0 and R γ4 from the edge curves γ0 and γ4 and by dividing their sum by two. In this, the respective radius Rγ0, Rγ4 originates from the centroid of the edge curve γ0, γ4.

As explained above, points of equal parameters of the curves γ1, γ2, γ3, γ4 are connected to each other, and to these are subsequently fitted one-dimensionally parameterized curves such as Bezier curves, whereby the tangentiality of the connectors computed in this manner relative to the 3D models 42, 44 is given by the edge curves γ0, γ4 and the associated reduced offset curves γ1, γ3.

Moreover, with regard to the intermediate element or pontic of the restoration to be manufactured, one takes into account the shape of the gingiva 122, which is scanned beforehand. During this, the 3D model of the pontic computed from the library data is distorted along the gingival direction in such a manner that a minimum spacing is maintained. This spacing should be in the region of 2 mm.

What is claimed is:

1. A CAD/CAM method for designing a connector between one first and one second element of a dental restoration, where for generating data required for the production of the connector, the connector is designed comprising the steps of:
   computing a first model of the first element and a second model of the second element;
   defining a connecting straight line between the first model and the second model;
   computing edge curves (γ0, γ4) on the first model and the second model, respectively, the edge curves being defined by the origins of surface normal vectors of the models, which satisfy boundary conditions relative to the connecting line;
   computing offset curves (γ1, γ3) on the first model and the second model, respectively, from the edge curves; and
   connecting the edge curves and the offset curves of the first model and the second model, and computing the connector on the basis of the path of the connection between the curves.

2. The method of claim 1, additionally comprising specifying a third curve (γ2), pierced by the connecting straight line, between the first model and the second model, wherein the connector has a course aligned to the connections between the first edge curves, the offset curves, and the third curve.

3. The method of claim 2, wherein the third curve (γ2) possesses a circular shape, having a center which is passed by a second centroid-connecting straight line, which extends between the centroids of the edge curves or of the surfaces enclosed by the edge curves.

4. The method of claim 3, wherein the third curve is pierced by the second centroid-connecting straight line, said second centroid-connecting straight line extending between the centroids of the edge curves or of the surfaces enclosed by the edge curves, whereby a third curve is pierced by the second centroid-connecting straight line in the middle between the centroids.

5. The method of claim 4, wherein the third curve is located in a plane, which is defined by vectors that originate in centers of additional third centroid-connecting straight lines, which extend between centroids of equal segments of the edge curves or of surface regions of the surfaces of the first and second model enclosed by the edge curves.

6. The method of claim 5, wherein each edge curve is subdivided into three equal segments, and from each segment centroid originates one of the third centroid-connecting straight lines.

7. The method of claim 3, wherein the radius of the third curve substantially corresponds to one half of the sum of average radii of the edge curves of the first and second models.

8. The method of claim 2, wherein the third curve (γ2) possesses a geometry different from that of a circle.

9. The method of claim 8, wherein the third curve possesses polygonal geometry.

10. The method of claim 1, wherein as boundary condition for the position of the origin of the surface normal vector defining the edge curve (γ0, γ4), one specifies an angle α between the connecting straight line and the surface normal vector.

11. The method of claim 1, wherein as boundary condition for the position of the origin of the surface normal vector defining the edge curve (γ0, γ4), one specifies a facing distance to be maintained relative to a preparation margin of at least one of the first and second elements.

12. The method of claim 1, wherein as boundary condition for the position of the origin of the surface normal vector defining the edge curve (γ0, γ4), one specifies an angle α between the surface normal vector and the connecting straight line as well as an angle β, which extends between the connecting straight line and a line extending between the origin of the surface normal vector and a characteristic point of the first or second model, whereby $(\alpha+\beta): 2 \approx \phi$ with $30° \leq \phi 90°$.

13. The method of claim 12, wherein $70° \leq \phi \leq 90°$.

14. The method of claim 12, wherein the characteristic point is the centroid.

15. The method of claim 1, wherein the connecting straight line between the first and the second model passes through at least one of their centroids, pseudo-rotation axes, and principal axes of inertia.

16. The method of claim 1, wherein at least one element is a pontic, and data for position and size of the pontic for the dental restoration to be produced are retrieved from a data library and subsequently, a connecting straight line is specified.

17. The method of claim 1, including the steps of:
scanning a physical model of a stump,
computing a three-dimensional model from the measured point distribution acquired by the scanning,
computing from the three-dimensional model, a three-dimensional model of a coping as the first or second model,
parameterizing the three-dimensional coping model in a two-dimensional parameter space, in which each point corresponds to an X, Y, Z coordinate and a normal vector in the three-dimensional space of the coping, and
determining the first edge curve from the parameterized two-dimensional space.

18. The method of claim 1, including the steps of:
computing a three-dimensional model as the first or second model of a pontic selected from a library,
parameterizing the three-dimensional model in a two-dimensional parameter space, in which each point corresponds to one X, Y, Z coordinate and one normal vector in the three-dimensional space, and
determining the edge curve from the parameterized two-dimensional space.

19. The method of claim 18, wherein rounding radii between the connector and the first or second element are computed from the course of the edge curve and the offset curve computed therefrom.

20. The method of claim 1, for producing a pontic and taking into account the shape of the gingiva such that the gingiva side of the pontic maintains a minimum distance to the gingiva.

21. A CAD/CAM method for designing a connector between one first and one second element of a dental restoration, where for generating data required for the production of the connector, the connector is designed comprising the steps of:
computing a first model of the first element and a second model of the second element;
defining a connecting straight line between the first model and the second model;
computing edge curves (y0, y4) on the first model and the second model, respectively, the edge curves being defined by the origins of surface normal vectors of the models, which satisfy boundary conditions relative to the connecting line;
computing offset curves (y1, y3) on the first model and the second model, respectively, from the edge curves; and
connecting the edge curves and the offset curves of the first model and the second model, and computing the connector on the basis of the path of the connection between the curves,
wherein as boundary condition for the position of the origin of the surface normal vector defining the edge curve (y0, y4), one specifies an angle α between the surface normal vector and the connecting straight line as well as an angle β, which extends between the connecting straight line and a line extending between the origin of the surface normal vector and a characteristic point of the first or second model, whereby $(\alpha+\beta): 2 = \phi$ with $30° \phi \leq 90$.

* * * * *